US 6,378,526 B1

(12) United States Patent
Bowman et al.

(10) Patent No.: US 6,378,526 B1
(45) Date of Patent: Apr. 30, 2002

(54) METHODS OF OPHTHALMIC ADMINISTRATION

(75) Inventors: Lyle M. Bowman, Pleasanton; James F. Pfeiffer, Oakland; Leslie A. Clark, Alameda, all of CA (US); Karl L. Hecker, Keene, NH (US)

(73) Assignee: InSite Vision, Incorporated, Alameda, CA (US)

( * ) Notice: Subject to any disclaimer, the term of this patent is extended or adjusted under 35 U.S.C. 154(b) by 0 days.

(21) Appl. No.: 09/127,920

(22) Filed: Aug. 3, 1998

(51) Int. Cl.[7] ............................................... A61B 19/00
(52) U.S. Cl. ...................................... 128/898; 604/521
(58) Field of Search ........................... 604/521; 128/898

(56) References Cited

U.S. PATENT DOCUMENTS

| | | |
|---|---|---|
| 2,033,397 A | 3/1936 | Richman |
| 2,591,457 A | 4/1952 | Maynes |
| 2,760,483 A | 8/1956 | Tassicker |
| 3,626,940 A | 12/1971 | Zaffaroni |
| 3,890,970 A | 6/1975 | Gullen |
| 3,961,628 A | 6/1976 | Arnold |
| 4,186,448 A | 2/1980 | Brekke |
| 4,454,151 A | 6/1984 | Waterbury |
| 4,499,898 A | 2/1985 | Knepshield et al. |
| 4,534,348 A | 8/1985 | Fedorov et al. |
| 4,549,529 A | 10/1985 | White |
| 4,552,146 A | 11/1985 | Jensen et al. |
| 4,578,061 A | 3/1986 | Lemelson |
| 4,580,561 A | 4/1986 | Williamson |
| 4,688,570 A | 8/1987 | Kramer et al. |
| 4,759,746 A | 7/1988 | Straus |
| 4,853,224 A | 8/1989 | Wong |
| 4,863,457 A | 9/1989 | Lee |
| 4,957,117 A | 9/1990 | Wysham |
| 4,968,296 A | 11/1990 | Ritch et al. |
| 4,990,135 A | 2/1991 | Truesdale |
| 4,997,652 A | 3/1991 | Wong |
| 5,049,142 A | 9/1991 | Herrick, et al. |
| 5,152,769 A | 10/1992 | Baber |
| 5,164,188 A | 11/1992 | Wong |
| 5,167,641 A | 12/1992 | Schmitz |
| 5,207,660 A | 5/1993 | Lincoff |
| 5,273,530 A | 12/1993 | Del Cerro, et al |
| 5,279,265 A | 1/1994 | Klein et al. |
| 5,284,476 A | 2/1994 | Koch |
| 5,294,604 A | 3/1994 | Nussenblatt, et al |
| 5,314,419 A | 5/1994 | Pelling |
| 5,336,178 A | 8/1994 | Kaplan et al. |
| 5,342,377 A | 8/1994 | Lazerson |

(List continued on next page.)

FOREIGN PATENT DOCUMENTS

| | | |
|---|---|---|
| DE | 2 148 700 | 5/1973 |
| EP | 0 022 977 | 1/1981 |
| WO | WO 92 08406 A | 5/1992 |
| WO | WO 92/19296 | 11/1992 |
| WO | WO 95/07722 | 3/1995 |
| WO | WO 95/32756 | 12/1995 |
| WO | WO 96 09838 A | 4/1996 |
| WO | WO 97 41844 A | 11/1997 |

OTHER PUBLICATIONS

Verbeek, A.M., et al., "Recurrent intrascleral cyst after strabismus surgery," *Graef's Arch Clin Exp Ophthalmol*, 234:S 229–S 231 (1996). (Abstract previously submitted).

*Primary Examiner*—Corrine McDermott
*Assistant Examiner*—Thomas C. Barrett
(74) *Attorney, Agent, or Firm*—Arnold & Porter

(57) ABSTRACT

Intrascleral injection of a therapeutic or diagnostic material at a location overlying the retina provides a minimally invasive technique for delivering the agent to the posterior segment of the eye. The procedure also allows for close proximity of the material to the targeted site and can be effectively used to treat conditions associated with the posterior segment of the eye, including macular degeneration, vein occlusion, and diabetic retinopathy.

29 Claims, 1 Drawing Sheet

U.S. PATENT DOCUMENTS

| | | |
|---|---|---|
| 5,370,607 A | 12/1994 | Memmen |
| 5,391,174 A | 2/1995 | Wetson |
| 5,409,457 A | 4/1995 | Del Cerro et al. |
| 5,419,777 A | 5/1995 | Hofling |
| 5,437,640 A | 8/1995 | Schwab |
| 5,443,505 A | 8/1995 | Wong, et al. |
| 5,454,796 A | 10/1995 | Krupin |
| 5,496,329 A | 3/1996 | Reisinger |
| 5,499,991 A | 3/1996 | Garman et al. |
| 5,538,054 A | 7/1996 | Linden et al. |
| 5,562,691 A | 10/1996 | Tano et al. |
| 5,562,693 A | 10/1996 | Devlin et al. |
| 5,609,574 A | 3/1997 | Kaplan et al. |
| 5,630,827 A | 5/1997 | Vijfvinkel |
| 5,632,984 A | 5/1997 | Wong, et al. |
| 5,643,292 A | 7/1997 | Hart |
| 5,674,240 A | 10/1997 | Bonutti et al. |
| 5,702,414 A | 12/1997 | Richter et al. |
| 5,707,643 A | 1/1998 | Ogura, et al. |
| 5,713,860 A | 2/1998 | Kaplan et al. |
| 5,746,716 A | 5/1998 | Vigil et al. |
| 5,767,079 A | 6/1998 | Glaser, et al. |
| 5,770,589 A | 6/1998 | Billson, et al. |
| 5,837,680 A * | 11/1998 | Moses et al. .................. 514/12 |
| 5,911,707 A | 6/1999 | Wolvek et al. |

* cited by examiner

METHODS OF OPHTHALMIC ADMINISTRATION

BACKGROUND OF THE INVENTION

1. Field of the Invention

The present invention relates to methods of ophthalmic administration. Specifically, the methods relate to intrascleral injection of therapeutic or diagnostic materials.

2. Description of the Related Art

Delivering therapeutic or diagnostic agents to the posterior segment of the eye, especially to the retina, macula, etc., poses several challenges. Topical instillation of an agent to the front of the eye such as by eye drops, generally provides low amounts of the agent (including none) to the posterior portion of the eye, due in part to poor diffusion through the various layers as well as the natural clearing processes encountered. Providing effective amounts of an agent to, for example, the retina via topical instillation is generally not possible given the distance and number of layers between the deposit site of the agent and the site to be treated. Another potential shortcoming with topical instillation is that the composition tends to be quickly removed from the eye by tears and other natural clearing processes. The resulting short duration of contact can further limit the likelihood of an appreciable amount of the agent reaching the posterior segment.

Conversely, systemic delivery of an agent to the posterior segment of the eye such as by oral administration, is limited by the blood-retinal barrier. The barrier limits the size and amount of agents that can reach the choroid and retina. Moreover, because the agent is systemically delivered, the dosage is limited so as not to provide a toxic dose of the agent to other parts of the body. This is especially a concern in treating chronic disorders where a long term dosing regimen is typically required. For this reason, overcoming the barrier by administering higher doses of the agent is usually not a practical alternative. Likewise, the risk of side effects is increased with systemic delivery.

Other proposals for delivering agents to the eye include the use of inserts and implants which release the agent over time onto or into the eye. An insert, as used in this application, is a device inserted over the eye, such as on the conjunctival layer, and generally comprises a polymer matrix containing an active agent. The agent that is released from the insert can diffuse through the sclera and into the eye. While sustained or long term agent contact with the eye can be achieved by this method, little if any of the agent reaches the posterior segment of the eye for much the same reasons as topical instillation. Implants are devices similar to inserts but they are surgically placed within the eye. Accordingly, implants bring the risk of infection and other problems due to its more invasive nature.

For example, U.S. Pat. No. 4,863,457 to Lee relates to an implant having a stem and base wherein the stem releases a drug and is positioned to extend into a canal, passageway, or orifice of the eye. The implant is taught to serve two functions: internal delivery of drug and mechanical prevention of passageway closure. The drawings illustrate placing the base of the implant in the subconjunctival space, or within the sclera itself, with the stem extending into the anterior chamber. The implant is taught to be especially useful in post-operative glaucoma patients as the drugs released can suppress scar tissue around the stem while the stem structure helps to maintain a passageway from the anterior chamber to Schlemm's canal. In this way, the implant is taught to ensure continued drainage of the aqueous humor from the anterior chamber and prevent a recurrence of the pressure buildup caused by glaucoma.

However, this implant is directed to treating the anterior chamber and not the posterior segment of the eye. Indeed, the option of inserting the implant into the sclera is problematic if attempted in the posterior segment of the eye. Here, partially cutting the sclera where it overlies the retina and inserting the base and stem of the implant therein, raises the risk of retinal detachment and choroidal hemorrhage. Only in the front of the eye, where the sclera does not overlie the retina and the vasculature of the choroid is low, can the partial thickness sclera flap technique be practically performed. Accordingly, the design and placement of this implant is not effective for delivering an agent to the posterior portion of the eye.

U.S. Pat. No. 5,707,643 to Ogura et al. relates to a biodegradable scleral plug that is inserted through an incision in the sclera into the vitreous body. The plug releases a drug into the vitreous body for treating the retina. The path of the plug is not, however, indicated. Assumedly, the plug would extend through the avascular region of the pars plana so as not to rupture any significant blood vessels or the retina. The drug will be applied to the entire retina by diffusion through the vitreous body, thus precluding the ability to provide a more concentrated application of the drug to one portion of the retina. Also, the invasive nature of the plug brings various risks including the risk of infection.

U.S. Pat. No. 5,443,505 to Wong et al. relates to implants that are taught to deliver drug to a localized site. The implants are typically placed in the suprachoroidal space over an avascular region of the eye such as the pars plana or a surgically induced avascular region. Another embodiment involves forming a partial thickness scleral flap over an avascular region, inserting the implant onto the remaining scleral bed, optionally with holes therein, and suturing closed the flap. The drug diffuses into the vitreous region and the intraocular structure. Locating the implant close to the back of the eye is apparently not possible as the region would not be avascular, unless surgery is performed to make an avascular region. Such removal is normally undesirable since vision loss will be induced.

Another delivery approach is direct injection. For the posterior segment of the eye, an intravitreal injection has been used to deliver drugs into the vitreous body. U.S. Pat. No. 5,632,984 to Wong et al. relates to the treatment of macular degeneration with various drugs by intraocular injection. The drugs are preferably injected as microcapsules. The intraocular injection into the posterior segment is taught to allow diffusion of the drug throughout the vitreous, the entire retina, the choroid and the opposing sclera. Similarly, U.S. Pat. No. 5,770,589 to Billison et al. relates to treating macular degeneration by intravitreally injecting an anti-inflammatory into the vitreous humor. These invasive injections are normally administered through the pars plana in order to minimize the damage to the eye. While drug is delivered to the posterior segment, it is not specifically administered to a target area such as the macula, but rather is supplied to the entire posterior segment. Additionally, the procedure has a high risk of infection and retinal detachment and has restricted use.

U.S. Pat. No. 5,767,079 to Glaser et al. relates to the treatment of ophthalmic disorders including macular holes and macular degeneration, by administration of TGF-β. The method of administration varies depending upon the nature and location of the pathology. The patent contemplates placing an effective amount of the growth factor on the ophthalmic abnormality. In treating the macula and retina, the examples teach that a surgical procedure involving a core vitrectomy or a complete pars plana vitrectomy is performed before the growth factor can be directly applied. The patent does mention the possible use of, inter alia, an intrascleral injection. However, no specifics are given about such a procedure, nor is such a procedure well known in the art. Presumably, the patentee intended either administration to the sclera on the anterior segment of the eye at an avascular region or administration to the sclera behind the retina via a surgical procedure through the vitreous body, retina, and choroid. The former method will not provide a large amount of drug to the posterior segment, as discussed above with regard to topical instillation and implants. The latter method is a dramatic, highly invasive, technique that would be suitable only where partial vision loss has already occurred or was imminently threatened. Such a procedure carries a high risk of infection or retinal detachment as well as loss of vision and clearly is problematic for chronic administration.

U.S. Pat. No. 5,273,530 relates to the intraretinal delivery and withdrawal of samples and a device therefor. Unlike direct intraocular injection techniques, the method disclosed in this patent avoids the use of a pars plana incision and instead uses an insertion path around the exterior of the orbit. The device, having a curved handle and tip with a collar, allows a cannula to be inserted through the posterior sclera and down into the subretinal space without passing through the vitreous body. The collar is stated to regulate the penetration to the desired depth. The method is basically directed to supplying cells to and/or withdrawing samples from the subretinal space. However, the device is taught to be adjustable to any part of the eye including the scleral area, the choroidal area, the subretinal area, the retinal area and the vitreous area. In use, the disclosed subretinal delivery method presents a significant risk of causing choroidal hemorrhaging. It should be noted that although the approximate location of the cannula can be observed through a slit lamp by tinting, the penetration of the cannula through the sclera and choroid can not be seen until the tip of the cannula penetrates the retinal surface.

The above methods show that delivering agents to the posterior segment of the eye, especially the back of the eye at the retina, macula, etc., is difficult. This region of the eye is isolated by both the anterior segment and the blood-retinal barrier. The techniques which are relatively easy to apply (topical instillation, oral administration) generally do not deliver a sufficient amount of the agent to the posterior segment and/or present toxicity or side effect problems. In contrast, techniques that deliver effective amounts (intravitreal injection) are complicated, invasive procedures that subject the patient to the risk of infection, retinal detachment, and further vision or eye damage. A minimally invasive method for delivering agents to the posterior segment of the eye would be of great benefit.

SUMMARY OF THE INVENTION

It is an object of the present invention to provide a method for administering agents to the eye.

It is another object of the present invention to provide a method for administering agents to the eye that is minimally invasive.

Preferred forms of the invention contemplated accomplish at least one of the above objects. One embodiment of the invention is a method of intrascleral injection, which comprises injecting into the scleral layer of an eye through a location on the exterior surface of the sclera which overlies retinal tissue an effective amount of a therapeutic or diagnostic material. The material or a component thereof will diffuse into the underlying tissue layers including the choroid and retina. By entering the sclera from the external side, the method avoids the invasiveness of the intravitreal injection technique, thereby reducing the risk of infection and allowing a regimen of treatments to be given throughout the year, if needed. Also, because the sclera moves with the entire eye including the retina, the site of deposit on the sclera will map to the corresponding point on the underlying retina, even as the eye moves within the eye socket. This means that site specific delivery can be achieved and maintained. Thus, by depositing material into the sclera at a site overlying the macula, the material will be easily delivered to the macula and surrounding tissues.

The injection procedure is not particularly limited and embraces the use of a cannula or needle as well as needleless particle/solution techniques. In a preferred embodiment, a cannula is inserted into the sclera in a rotational direction relative to the eye and not orthogonal to the surface of the sclera. By angling the cannula insertion into the sclera, the risk of accidentally perforating the sclera and causing damage to the underlying tissue (choroid and/retina) or hemorrhaging can be reduced or eliminated.

The present invention allows the delivery of a variety of agents to the posterior segment of the eye whenever such delivery would be desirable, including treating conditions of the posterior or anterior segments and diagnosing various conditions.

DETAILED DESCRIPTION OF THE INVENTION

Figure 1:
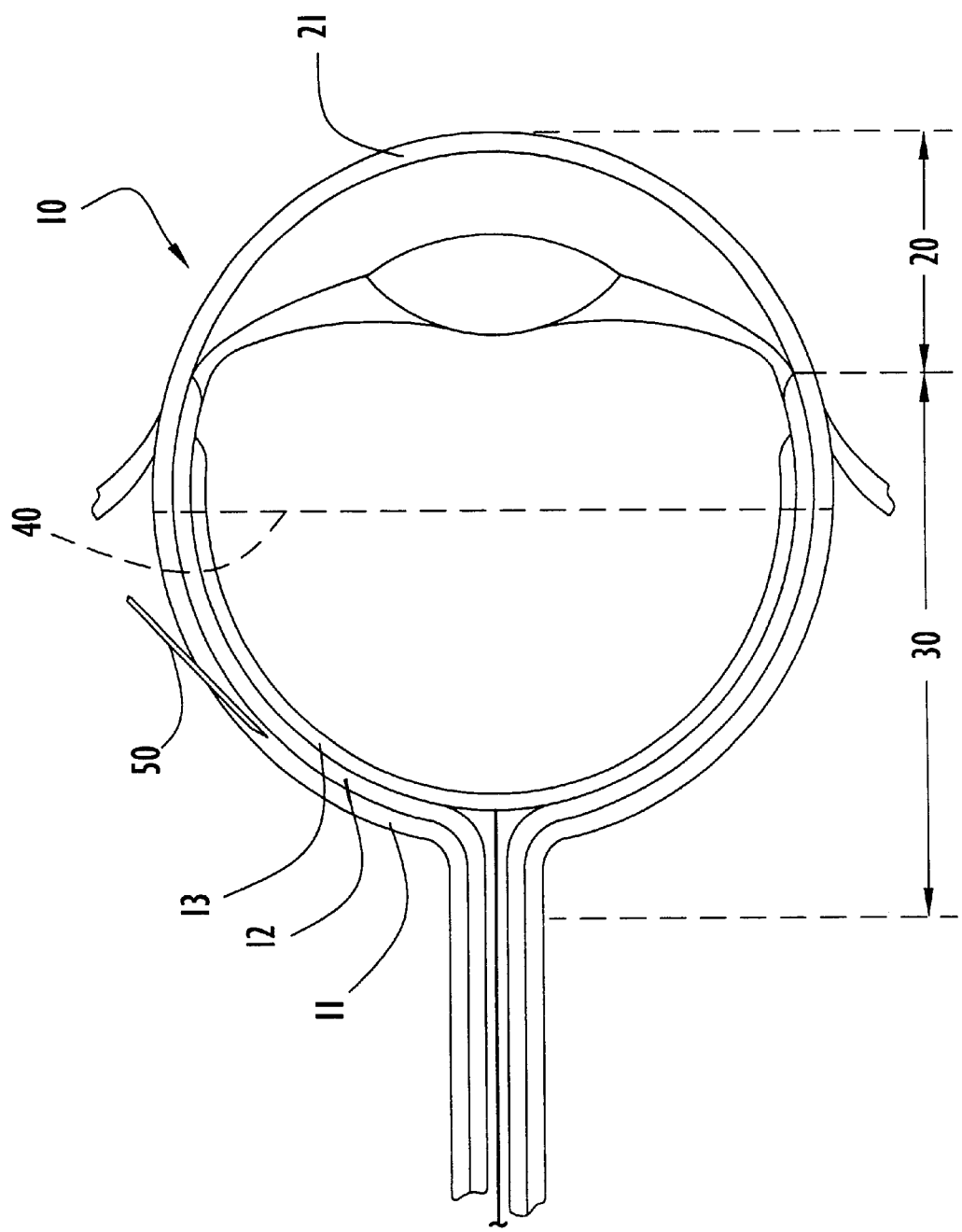
FIG. 1 illustrates an eye having a cannula inserted into the scleral in accordance with one embodiment of the present invention.

The present invention involves injecting a material into the sclera of an eye. The eye can be of any vertebrate animal including human and non-human mammals. The sclera is a thin, avascular layer, comprised of a highly ordered collagen network, that surrounds most of the vertebrate eye. The cornea replaces the sclera in the front of the eye, with the transition from sclera to cornea occurring at the limbus. Because the sclera is avascular, there is essentially no risk of hemorrhaging after an injection therein and the injected material is not rapidly removed or "cleared" from the eye. Thus the sclera can be effectively utilized in the present invention as a natural storage depot.

The material can be placed within the sclera by any suitable injection technique. Typically a cannula is inserted into the sclera and the therapeutic or diagnostic material is then injected through the cannula and into the scleral layer. Generally this type of injection uses a syringe or other piston-type mechanism, which can be operated either by hand or by an actuator. Alternatively, the material can be injected through the cannula by a pump, such as a metering pump. Other techniques include non-cannular injection methods, or so-called "needle-less injection" techniques, where gas pressure is used to force solutions or particles, or both, of material into the underlying tissue. For example, processes similar to the commercially available needle-less injectors for solutions, or for powders like the POWDER-JECT™ technology, can be used. Typically, such processes involve injecting particles larger than 20 to 40 microns directly or indirectly into the tissue by the use of high pressure gas. Particles may be larger or smaller depending upon the suitable application.

An embodiment of the present invention using a cannula is described below in greater detail and with reference to FIG. 1. Eye 10 (not drawn to scale) can be divided into an anterior segment 20 and posterior segment 30 with an equator 40. Sclera 11 covers the outside of the eye around the posterior segment and part of the anterior segment while cornea 21 covers the outer part of the remainder of the anterior segment. Underlying the sclera is choroid 12 and retina 13. A cannula 50 (shown here as a needle with a beveled terminal end) has been inserted into the sclera from a location on the external (or outer) surface of the sclera that overlies the retina. The cannula has been inserted in a substantially rotational direction meaning that the insertion path into the sclera generally points around the eye and not into the center of the eye. This is a preferred embodiment because it decreases the risk of accidentally penetrating through the sclera and into the choroid or retina. Obviously, inserting a cannula, especially a sharpened or beveled cannula, into the vascular choroid or light sensitive retina can cause serious injury to these layers with resulting vision impairment. Generally insertion of the cannula in a "substantially rotational direction" will be performed at an insertion angle of less than about 60 degrees; the "insertion angle" being defined by the angle formed between the tangent to the sclera at the external point of entry and the insertion path of the cannula into the sclera (or in the case of a curved cannula, the tangent to the curved cannula insertion path at the entry point into the sclera). Preferably the insertion angle is less than 50, more preferably from about 20 to about 40 degrees. In one embodiment the insertion angle is about 30 degrees.

In a preferred embodiment, the cannula is inserted in an orientation to the sclera such that it must exit the sclera, if at all, through another location on the exterior surface of the sclera: hereinafter a "fail safe orientation." This can be accomplished, for example, by inserting a straight cannula at a sufficiently low insertion angle. Because the sclera is curved, the cannula can be angled so as to travel on a path that is tangent to a point on the curving inner surface layer of the sclera. At all lower angles, the closest the cannula will come to the inner surface of the sclera is above the tangent point. Further extending the cannula beyond this point will bring the leading end of the cannula further away from the inner surface of the sclera and closer to the exterior surface of the sclera. Thus, the cannula will miss perforating the inner surface of the sclera no matter how far the cannula is extended. This provides a safer injection technique in that if the cannula is inserted "too far," the result is only that the injected material will not go into the sclera as intended, but instead will be deposited on the exterior of the sclera. Such injections into the external part of the eye should have no deleterious effect. Orienting the cannula, whether curved or straight, such that it enters the sclera from the exterior surface thereof and must exit the sclera, if at all, also through the exterior surface and not through the inner surface of the sclera, significantly reduces the risk of accidentally damaging the choroid or retina.

Inserting the cannula in a substantially rotational direction also allows for increased insertion distances of the cannula into the sclera which can increase the hydrodynamic seal between the cannula and the scleral tissue. In some embodiments, the cannula is preferably inserted into the sclera a distance that is greater than or equal to, the thickness of the sclera, preferably at least one and a half times the thickness, measured at the entry point on the exterior surface. This is particularly useful near the equator where the sclera is quite thin, but is not limited to such a region. By increasing the surface area between the cannula and the scleral tissue, a better hydrodynamic seal can be formed which allows for larger and/or faster injections.

The cannula is not particularly limited and need only fit within the thickness of the sclera at the point of entry. Preferably the cannula is sufficiently small in diameter that no hole is visible in the sclera upon macroscopic observation of the entry site after the injection. Typically, at least a 25 gauge, preferably at least a 28 gauge, more preferably about 30–33 gauge cannula is employed, but such is not required. The size of the cannula depends in part on the viscosity of the material to be injected, the amount of material to be injected, and the time of injection. A very fine gauge cannula, while causing little if any trauma to the eye, may not be able to allow sufficient flow of a particular material into the sclera and thus would not serve as a useful conduit. The above gauge sizes are, especially for humans, a size that typically accommodates these competing features. Preferably the cannula is sharp on its leading end (i.e. a needle) such as with a bevel or a hollow ground point. In some cases it may be desirable that the bevel engages the sclera in an upside down orientation whereby the leading edge of the bevel is adjacent to and makes first contact with the exterior surface of the sclera. This can aid in holding the cannula in alignment with the sclera as the cannula is inserted and prevent or reduce the risk of the cannula rotating the eye or sliding/skidding on the scleral tissue. The desirability of such an upside down bevel approach depends upon the insertion angle, the thickness of the sclera, the shape of the cannula and the size of the cannula.

The entry point on the exterior surface of the sclera overlies the retina and thus is in the posterior segment of the eye. It should be noted, however, that the injection of material into the sclera may occur at a location within the sclera that does not overlie the retina, depending upon the angle and direction of injection; e.g. in the case of a cannular injection in a substantially rotational direction, the injection site within the sclera may be anterior to the retina. Nonetheless, generally the injection site of the material within the sclera is also over the retina. Preferably the entry point and injection site are posterior to the area of eye muscle insertion, more preferably posterior to the equator of the eye, and more preferably more than 45 degrees posterior to the equator. Also, when a disease or condition is present or concentrated in a local area, such as macular degeneration, it is preferred to make the injection in the vicinity of the affected area. In this way, a depot of the injected material is formed within the sclera that is near the site to be treated and preferably a portion of the injected material at least partially overlies the localized area to be treated. Such can allow for more effective treatment and/or reduced amounts of material needed to be injected. Also, because the material is stored within the sclera, the material remains in proximity with the affected area regardless of eye movement.

The posterior segment can be reached in a number of ways. The eye can be rotated in order to expose the posterior segment. This is typically accomplished by holding the conjunctiva with forceps and rotating the eye so that the front of the eye moves downwardly (i.e. "rotated forwardly"). The eye can be rotated in other directions as appropriate and other techniques for rotation can be used as desired. Another technique involves using a curved handled device that can be inserted around the eye to position the cannula or other injection apparatus over the desired posterior location. The concept of such a device is shown in U.S. Pat. No. 5,273,530. While the device could be used as shown therein, it should preferably be modified so that the cannula is retractable and more preferably modified so that the cannula will be inserted in a substantially rotational direction.

Accessing the posterior of an eye also normally entails penetrating the conjunctiva. One way is to make an incision in the conjunctiva and insert the cannula or other injection apparatus through the incision to the sclera. Such a method works with both the eye rotating technique and the curved handle device technique discussed above for accessing the posterior segment of the eye. Such an incision is relatively non-invasive and is similar to conjunctival incisions (peritomy) that ophthalmologists make in carrying out other procedures. Another approach is to rotate the eye into the desired position and then inject through the conjunctiva and into the sclera. In the case of a cannular injection, this means inserting the terminal end of the cannula through the conjunctival layer and into the sclera. In this approach, it may be necessary to prevent movement of the conjunctiva relative to the sclera. This can be done by taking into account the relative looseness of the conjunctiva, the angle of insertion, the presence of a bevel and its orientation, and the use of conjunctiva holding or stabilizing devices or techniques. For example, holding a portion of the conjunctiva in place by physical restraint (e.g., friction or pins) while inserting the cannula can be effective in preventing relative movement between the conjunctiva and the sclera.

The insertion of the cannula can be carried out by hand or with a device. In a preferred embodiment of the invention, the insertion is carried out using a guided injection device such as described in our co-pending U.S. patent application Ser. No. 09/127,919, filed on even date herewith and bearing attorney docket number 03654.0247, the entire contents of which are incorporated herein by reference. In general, a guided injection device has a mechanism for providing a needle at a predetermined angle of insertion and preferably a predetermined depth of insertion. For example, a device having a guide platform which comprises a support surface that conforms to the shape of the sclera and a channel extending through it for guiding the needle can be advantageously employed. When the support surface is contacted to the exterior surface of the sclera, the angle of the channel relative to the sclera is fixed. The needle transmitted through the channel will thus be inserted into the sclera at the predetermined insertion angle. Various mechanical means, such as a stop or collar, can be used to limit the insertion distance of the needle. The needle itself is connected to the material to be injected, such as by directly attaching to a reservoir on the device or to a remote reservoir, so as to facilitate the injection step. For safety the needle is preferably retractable such that after injection of the material, the needle can be withdrawn back within the device, behind the support surface. Actuators for achieving the back and forth movement of a needle are well known in the art. Such a guide platform can be placed on the distal end of the device shown in U.S. Pat. No. 5,273,530, and thus, with an appropriate predetermined angle of insertion, make the blind insertion of a needle into the sclera at the back of the eye a safe procedure.

The material to be injected can be any material having a therapeutic or diagnostic utility or purpose. The material can be a gas, a liquid, a suspension, a powder, etc., so long as it is injectable. Preferably, the material is injectable through a cannula. Typically the materials injected in the present invention are similar to intravitreal and intramuscular injection formulations in terms of concentrations, viscosities, adjuvants, etc., although such is not required. A large number of diagnostic and therapeutic materials are well known in the art for treating various ocular diseases and conditions, as is their preparation and formulation, and all such materials are specifically contemplated for use in the present invention.

A "therapeutic material" means a material that provides a healing, restraining or prophylactic effect to a disease or condition or which suppresses, ameliorates or prevents the symptoms associated with a disease or condition. The material can be a single substance or a combination of substances. Typically, a therapeutic material is a composition containing a pharmaceutically active agent and an ophthalmologically acceptable carrier or diluent. The active agent useful in the present invention include all ophthalmologically effective agents, examples of which include anti-angiogenesis agents such as metalloproteinase inhibitors, vascular endothelium growth factor (VEGF) regulating agents, fibroblast growth factor (FGF) regulating agents, integrin blockers, protein kinase C inhibitors, and endogenous angiogenesis inhibitors (e.g., angiostatin); ischemic/reperfusion preventing agents such as NMDA receptor antagonists, AMPA receptor antagonists, antioxidants, peroxidation inhibitors, apoptosis inhibitors, adenosine or adenosine regulating agents, calcium channel blockers, and nitric oxide regulating agents; anti-inflammatory agents such as steroidal and non-steroidal anti-inflammatory agents; antiviral agents; antioxidants; antibiotics; antitumor agents such as tumor necrosis factors; anti-cataract agents; anti-glaucoma agents; anesthetics; gene therapy compositions such as triplex nucleic acids and ribozymes; antibodies and fragments thereof; and antisense compounds.

Specific examples of useful active agents include, but are not limited to, pilocarpine, timolol, atenolol, betaxolol, levobunolol, tetracycline, hydrocortisone, prednisolone, prednisone, dexamethasone, progesterone, fluorometholone, lazaroids and 21-aminosteroid compounds as disclosed in U.S. Pat. No. 5,124,154 (incorporated herein by reference), aspirin, benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketorolac, ketoprofen, lactorolac, lonazolac, metiazinic, miroprofen, naproxen, oxaprozin, oxepinac, phenacetin, pirprofen, pirazolac, protizinic acid, sulindac, suprofen, tiaprofenic acid, tolmetin, zomepirac, tolrestat, lisinopril, statil, retinoic acid, methotrexate, mitomycin, urokinase, streptokinase, cephaloridine, chloramphenicol, clindamycin, tobramycin, penicillin, ampicillin, erythromycin, streptomycin, neomycin, cyclosporine A, cyclosporine G, TGF-$\beta$, TGF-$\beta$2, TNF-$\alpha$, TNF-$\beta$, bFGF, and $\alpha$-2a interferon, anti-FGF antibody, anti-VEGF antibody, FGF antisense, VEGF antisense, VEGF receptor blockers, cysteine analogs, terilazad mesylate, angiostatin, endostatin, memantine, Cerestat, Batimastat, Marimastat, superoxide dismutase, GEM-antisense compounds, and Lexipafant.

One advantage of the present invention is the ability to use enzyme-unstable agents. Because the sclera is avascular, enzymes that would normally attack and degrade certain proteins and other agents if placed intraocularly, will not generally reach the intrascleral depot formed by the present invention.

The active agent can be combined with a suitable carrier or diluent, if needed, as is well known in the art and includes aqueous as well as non-aqueous systems. The composition used in the present invention contains no physiologically or ophthalmologically harmful constituents. Typically purified or deionized water is used. The pH is adjusted as needed by adding any physiologically and ophthalmologically acceptable pH adjusting acids, bases or buffers. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. Salts and buffers would include citrate/dextrose, sodium bicarbonate, ammonium chloride and mixtures of the aforementioned acids and bases. The pH is typically in the neutral range such as from about 6 to about 8, but is not limited thereto. Non-aqueous systems include the use of known ophthalmologically acceptable oils such as polyethylene glycols and silicone oils. The active agent can be in solution, in suspension, or both. If the active agent is in solid form, its particle size should be sufficiently limited to permit injection (e.g., the agent is able to pass through a cannula) and so as not to cause irritation to the eye once injected.

In a preferred embodiment, the composition contains a component that facilitates or improves the sustained release of the active agent as is known in the art. For example, incorporating a polymeric suspending agent can provide sustained release. The polymer should be biodegradable or biocompatible such that it can be cleared from the eye by natural transport effects. The active ingredient can be incorporated into the polymer matrix, adsorbed on the polymer surface, encapsulated within a polymer coating, etc. as are well known in the art. Examples of suitable polymers include water-soluble polymers such as dextran, polyethylene glycols, polyvinylpyrolidones, polysaccaride gels, Gelrite®, cellulosic polymers like hydroxypropyl methylcellulose and carboxymethylcellulose, hyaluronic acid polymers, and poly(lactic acid) and copolymers of lactic acid and one or more of glycolic acid, malic acid, glyceric acid, and tartaric acid. Carboxy-containing polymers such as uncrosslinked polyacrylic acids and copolymers thereof are also useful as suspending agents for insuring sustained release. Crosslinking is permissible only to the extent that the polymer can clear; i.e., crosslinking generally prevents biodegredation and thus the entire polymer must be susceptible of being cleared from the eye. Other forms include liposomes and lipid emulsions.

The composition should contain a sufficient amount of active ingredient to achieve the desired effect as can be readily determined by workers skilled in the art. In general, the solubility of the active ingredient in water and the concentration of the active ingredient needed in the tissue, guide the amount and rate of release of the agent. It should be borne in mind that the sclera is a depot of limited size and the concentration of the agent may need to reflect this. In general the amount of material to be injected is at least 0.1 $\mu$l, typically from around 0. 1 to 25 $\mu$l, more typically from about 1 to 25 $\mu$l, such as from about 3 to about 25 $\mu$l or from about 3 to 10 $\mu$l. If more material is needed then can be practically delivered in a single injection, then multiple injections can be performed; i.e., injecting 6 $\mu$l of therapeutic material in three different sites within the sclera during a single office visit.

Other components of the therapeutic material include solubilizers, stabilizers, preservatives, and other ingredients as are well known in the ophthalmology art. If the composition is supplied as a ready to inject single dose, then a preservative is typically omitted. The composition can be provided as a frozen liquid or as a lyophilized powder for reconstituting.

Diagnostic materials include a gas and dye solutions. For example, a gas such as nitrogen, air, or other inert gas, can be supplied in order to inflate the area and aid in some types of diagnostic procedures; i.e., improving the image in an ophthalmoscope. Similarly, a dye can be injected in order to aid in diagnosing various conditions by providing higher contrast and/or a staining pattern.

The rate of injection of the material via a cannula into the sclera is dependent on several factors including the viscosity of the material and the duration of the injection and can be readily determined by workers of ordinary skill in the art. Typically the injection rate is from about 0.1 to about 3.0 $\mu$l/s, preferably from about 0.5 to 1.0 $\mu$l/s. Injections typically will last for up to 10 seconds, although longer injection times are possible, especially with the use of a hand rest/support, and are contemplated by the present invention. Another consideration is the degree of hydrodynamic seal around the cannula. Too high of an injection rate or pressure may cause the material to flow out of the sclera along the sides of the cannula with very little of the material being lodged within the sclera. One way to improve the hydrodynamic seal is to increase the insertion length of the cannula into the sclera, as has been discussed above.

The present invention can be used to treat a variety of ocular diseases or conditions including, but not limited to, cystoid macular edema, age-related macular degeneration, diabetic retinopathy, diabetic maculopathy, central retinal artery occlusion, central retinal vein occlusion, branch retinal artery occlusion, branch retinal vein occlusion, retinopathy of prematurity, sickel cell retinopathy, photic retinopathy, radiation retinopathy, retinal detachment, retinitis pigmentosa, macular hole, cataract, and glaucoma as well as accidental or surgically induced trauma to the eye. Suitable therapeutic materials, known for treatment of an ocular disease or condition, especially a retinal disease or condition, can be injected into the sclera in close proximity to the affected site by the present invention to thereby provide effective treatment and enhanced delivery.

For example, one embodiment of the invention relates to treating neovascular diseases of the eye, such as diabetic retinopathy, macular degeneration, and neovascularization of the retina or choroid, by injecting into the sclera, through a location on the exterior surface of the sclera that overlies retinal tissue, an effective neovascularization reducing or preventing amount of an anti-angiogenesis agent. Such agents are described above and are generally well known in the art, including metalloproteinase inhibitors, vascular endothelium growth factor regulating agents, FGF regulating agents, integrin blockers, and protein kinase C inhibitors. The VEGF regulating agents include, without limitation, VEGF, antisense compounds thereof, antibodies thereof, and antibody fragments thereof having anti-angiogenesis activity. Antioxidants are also a highly useful class of compounds for treating these types of diseases.

With regard to macular degeneration, it is preferred that the insertion site is over the macula or in its immediate vicinity (e.g., more than 45 degrees posterior to the equator). More preferably, the insertion and injection steps provide at least a portion of the intrasclerally injected therapeutic material overlying the macula. The material to be injected can be any macular degeneration treating material. Specifically contemplated active agents include the above anti-angiogenesis compounds of VEGF, an antisense compound of VEGF, an antibody of VEGF, a fragment of an antibody of VEGF, triplex nucleic acids of VEGF, a receptor blocker for VEGF, and ribozymes for VEGF as well as antioxidants.

Another embodiment is treating cataracts. Although the disease manifests in the anterior segment, its root cause may lie in the posterior segment. Providing an antioxidant into the posterior segment can prevent or reduce cataracts. Here a preferred antioxidant is a 21-aminosteroid such as a lazaroid.

The following examples serve to illustrate the materials that can be injected by the present invention and should not be considered to limit the scope of the present invention.

EXAMPLE 1

An injectable therapeutic material containing the PAF antagonist Lexipafant (BB-882) is prepared as follows. In a 250-ml beaker, about 50 g of DI water is added and heated up to 80–90° C. on a hot plate while stirring with a magnetic stir bar. HPMC is dispersed into the hot water and stirred for 15 min. followed by cooling to RT while stirring. 10 g of room temperature water is then added to the polymer and stirred for 10 min. In a separate container, Pluronic F-127 and sorbitol are dissolved in 20 g of DI water. Glycerin is then added to the Pluronic F-127 solution and stirred until dissolve completely. The Pluronic F-127 solution is then added to the polymer suspension and stirred for 10 min. BB-882, dissolved in 1N HCl solution, is then added to the polymer mixture with stirring for 10 min. The pH of the resulting polymer mixture is adjusted to about 7.4 with 2N NaOH, stirred for 10 min., and then brought to 100% with q.s. of DI water. The formulation may be made sterile by heating the formulation to 123° C. for 30 minutes and sterile filtering the drug, NaOH, and residual water after heating. The 100 grams of material is summarized in the following table:

| COMPOSITION | % (Wt/Wt) |
|---|---|
| BB-882 | 1.0 |
| Hydroxylpropyl Methylcellulose, Type 2910, USP | 2.5 |
| Sorbitol, USP | 1.5 |
| Glycerin, USP | 1.0 |
| Pluronic F-127, NF | 1.0 |
| Hydrochloric Acid, (1N solution) | 5.0 |
| Sodium Hydroxide, NF, 2N for pH adjustment | q.s. to pH 7.4 |
| Purified Water, USP | q.s. |

Total weight: 100 grams

EXAMPLE 2

In a manner similarly to that set forth in Example 1, the following materials can also be made:

| COMPOSITION | % (Wt/Wt) |
|---|---|
| BB-882 | 0.1 |
| Hydroxylpropyl Methylcellulose, Type 2910, USP | 2.5 |
| Sorbitol, USP | 1.5 |
| Glycerin, USP | 0.2 |
| Edetate Disodium, USP | 0.10 |
| Sodium Chloride, USP | 0.32 |
| Sodium Hydroxide, NF, 2N for pH adjustment | q.s. to pH 6 |
| Purified Water, USP | q.s. |

Total weight: 100 grams

EXAMPLE 3

In a manner similarly to that set forth in Example 1, the following materials can also be made:

| COMPOSITION | % (Wt/Wt) |
|---|---|
| Diclofenac Na, USP | 0.1–1.0 |
| Hydroxylpropyl Methylcellulose, Type 2910, USP | 2.5 |
| Mannitol, USP | 1.5 |
| Sodium Chloride, USP | 0.21 |
| Poloxamer 407, NF | 0.05 |
| Boric Acid, USP | 0.5 |
| Magnesium Chloride, USP | 0.05 |
| Sodium Hydroxide, NF, 2N for pH adjustment | q.s. to pH 6 |
| Purified Water, USP | q.s. |

Total weight: 100 grams

EXAMPLE 4

Lazaroids are known to be potentially useful in treating a variety of ocular ischemic diseases such as glaucoma and diabetic retinopathy. Suitable formulations may be generally formulated as follows. 0.005 grams of the aminosteroid is dissolved into a saline solution formed of 0.9 grams of sodium chloride dissolved in intravenous grade water. The pH is then adjusted to 7.4 with NaOH and the total weight adjusted with water to 100 grams. The mixture is then sterilized. Alternatively, if the aminosteroid is not a powder, but is a lipid emulsion or in a liposome, it can be dispersed in the saline solution. A suspension can be made by adding hyaluronic acid such as sodium hyaluronate, or other suitable polymer, typically about 1.0 grams and with an increase in the amount of the agent, such as to 0.05 grams. The suspension need only remain sufficiently viscous to allow injection. Suitable aninosteroids include U-74006F, U-74500A, and U-75412A.

Another formulation is to slowly add 10 grams of U-74006F to 950 ml of pure water having 20 millimoles of citric acid under an inert atmosphere and with stirring. Three millimoles of sodium citrate and 8 millimoles of sodium chloride are added with stirring until a clear solution is obtained. The solution can then be sterilized.

EXAMPLE 5

An injectable therapeutic material containing Batimastat (BB-94) is prepared as follows. In a 250-ml beaker, about 50 g of DI water is added and heated up to 80–90° C. on a hot plate while stirring with a magnetic stir bar. HPMC is dispersed into the hot water and stirred for 15 min. followed by cooling to RT while stirring. 10 g of room temperature water is then added to the polymer and stirred for 10 min. In a separate container, Pluronic F-127 and sorbitol are dissolved in 20 g of DI water. Glycerin is then added to the Pluronic F-127 solution and stirred until dissolve completely. The Pluronic F-127 solution is then added to the polymer suspension and stirred for 10 min. BB-94 is then added to the polymer mixture with stirring for 10 min. The pH of the resulting polymer mixture is adjusted to about 6.0 with 2N NaOH, stirred for 10 min., and then brought to 100% with q.s. of DI water. The formulation may be made sterile by heating the formulation to 123° C. for 30 minutes and sterile filtering the drug, NaOH, and residual water after heating. The 100 grams of material is summarized in the following table:

| COMPOSITION | % (Wt/Wt) |
|---|---|
| BB-94 | 0.3 |
| Hydroxylpropyl Methylcellulose, Type 2910, USP | 2.5 |
| Sorbitol, USP | 1.5 |
| Glycerin, USP | 1.0 |
| Pluronic F-127, NF | 1.0 |
| Sodium Hydroxide, NF, 2N for pH adjustment | q.s. to pH 6.0 |
| Purified Water, USP | q.s. |

Total weight: 100 grams

The invention having been thus described, it will be obvious that the same may be varied in many ways without departing from the scope and spirit of the invention as defined by the following claims.

We claim:

1. A method of intrascleral injection, which comprises:

injecting with a cannula an effective amount of a therapeutic or diagnostic material into the scleral layer of an eye; wherein said cannula is inserted through a location on an exterior surface of the sclera over the posterior segment of the eye.

2. The method according to claim 1, further comprising inserting said cannula into said scleral layer in a substantially rotational direction.

3. The method according to claim 1, wherein said cannula is inserted into said scleral layer a distance greater than the thickness of the sclera at the location of insertion.

4. The method according to claim 1, wherein said insertion is carried out using a guided injection device.

5. The method according to claim 2, wherein said cannula is inserted at an insertion angle of less than about 60 degrees.

6. The method according to claim 5, wherein said cannula is inserted at an insertion angle of from about 20 to 40 degrees.

7. The method according to claim 2, wherein said cannula is inserted in a fail safe orientation.

8. The method according to claim 1, wherein the amount of material injected is at least 0.1 µl.

9. The method according to claim 8, wherein the amount of material injected is within the range of about 3 to about 25 µl.

10. The method according to claim 1, wherein the material is injected at a rate of from about 0.1 to about 3.0 µl/s.

11. The method according to claim 1, wherein the material comprises a pharmaceutically active agent and an ophthalmologically acceptable carrier.

12. The method according to claim 11, wherein said ophthalmologically acceptable carrier is water or oil.

13. The method according to claim 11, wherein said pharmaceutically active agent is selected from the group consisting of metalloproteinase inhibitors, vascular endothelium growth factor regulating agents, fibroblast growth factor regulating agents, integrin blockers, protein kinase C inhibitors, endogenous angiogenesis inhibitors, calcium channel blockers, NMDA receptor antagonists, AMPA receptor antagonists, antioxidants, peroxidation inhibitors, apoptosis inhibitors, adenosine or adenosine regulating agents, nitric oxide regulating agents, anti-inflammatory agents, antiviral agents, antibiotics; antitumor agents, anticataract agents, anti-glaucoma agents, anesthetics, antibodies and fragments thereof, antisense compounds, ribozymes, and triplex nucleic acids.

14. The method according to claim 11, wherein said material further comprises a biodegradable polymer matrix.

15. The method according to claim 1, wherein said injection is made posteriorly to the equator of the eye.

16. The method according to claim 15, wherein said location of said insertion substantially overlies the macula or its immediate vicinity.

17. The method according to claim 1, further comprising, making an incision in a conjunctival layer and passing said cannula through said incision, prior to said injecting step.

18. The method according to claim 1, wherein the terminal end of said cannula penetrates a conjunctival layer before entering said scleral layer.

19. The method according to claim 1, further comprising repeating said injecting at one or more locations on said scleral layer.

20. The method according to claim 1, wherein said eye is suffering from an ocular disease and said material is a therapeutic material effective for treating said disease.

21. The method according to claim 20, wherein said disease is selected from the group consisting of cystoid macular edema, age-related macular degeneration, diabetic retinopathy, diabetic maculopathy, central retinal artery occlusion, central retinal vein occlusion, branch retinal artery occlusion, branch retinal vein occlusion, retinopathy of prematurity, sickel cell retinopathy, photic retinopathy, radiation retinopathy, retinal detachment, retinitis pigmentosa, macular hole, cataract, and glaucoma.

22. The method according to claim 21, wherein said disease is diabetic retinopathy and said therapeutic material comprises an anti-angiogenesis agent.

23. The method according to claim 21, wherein said disease is glaucoma.

24. A method for treating macular degeneration, which comprises injecting an effective macular degenerative treating amount of an agent into the sclera of an eye in need of treatment thereof through a location on the exterior surface of the sclera over the posterior segment of the eye.

25. The method according to claim 24, wherein said anti-macular degenerative agent is selected from the group consisting of antisense compounds of VEGF, antibodies of VEGF, a fragment of an antibody of VEGF, triplex nucleic acids of VEGF, receptor blockers for VEGF, ribozymes for VEGF and antioxidants.

26. The method according to claim 24, wherein said agent is injected into a portion of the sclera that substantially overlies the macula or its immediate vicinity.

27. A method for treating a condition in the eye involving neovascularization, which comprises injecting into the sclera, through a location on the exterior surface of the sclera over the posterior segment of the eye, an effective neovascularization reducing or preventing amount of an anti-angiogenesis agent.

28. The method according to claim 27, wherein said agent is selected from the group consisting of metalloproteinase inhibitors, VEGF regulating agents, FGF regulating agents, integrin blockers, and protein kinase C inhibitors.

29. The method according to claim 27, wherein said condition is diabetic retinopathy.

* * * * *